(12) United States Patent
Nagasaka (10) Patent No.: US 9,351,651 B2
(45) Date of Patent: May 31, 2016

(54) MAGNETIC FIELD MEASUREMENT APPARATUS

(71) Applicant: SEIKO EPSON CORPORATION, Tokyo (JP)

(72) Inventor: Kimio Nagasaka, Hokuto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 48 days.

(21) Appl. No.: 14/159,925

(22) Filed: Apr. 2, 2014

(65) Prior Publication Data

US 2014/0206981 A1 Jul. 24, 2014

(30) Foreign Application Priority Data

Jan. 21, 2013 (JP) .................................. 2013-008648

(51) Int. Cl.
*A61B 5/05* (2006.01)
*A61B 5/04* (2006.01)
*G01R 33/032* (2006.01)

(52) U.S. Cl.
CPC .......... *A61B 5/04008* (2013.01); *G01R 33/032* (2013.01)

(58) Field of Classification Search
CPC ..................... A61B 5/04008; G01R 33/032
See application file for complete search history.

(56) References Cited

U.S. PATENT DOCUMENTS

| 8,405,389 | B2 | 3/2013 | Sugioka et al. | |
|---|---|---|---|---|
| 2011/0101974 | A1* | 5/2011 | Nagasaka | ................... 324/244.1 |
| 2011/0193555 | A1* | 8/2011 | Sugioka et al. | ............ 324/244.1 |

FOREIGN PATENT DOCUMENTS

JP    A-2009-162554    7/2009

* cited by examiner

*Primary Examiner* — Mark Remaly
(74) *Attorney, Agent, or Firm* — Oliff PLC (57) ABSTRACT

A magnetic field measurement apparatus includes a probe beam irradiating unit that radiates a probe beam. A gas cell is arranged on an optical axis of the probe beam and shows a linear dichroism with respect to the probe beam between a first axis and a second axis. Another gas cell is arranged on the optical axis of the probe beam on the opposite side of the probe beam irradiating unit with respect to the gas cell, and shows a linear dichroism with respect to the probe beam between a third axis and a fourth axis, which are different from the first and the second axes. A measuring unit measures a difference between magnetic fields in the gas cells and on the basis of amounts of change of a plane of polarization of the probe beam that has passed through the gas cell and the gas cell.

6 Claims, 6 Drawing Sheets

MAGNETIC FIELD MEASUREMENT APPARATUS

The entire disclosure of Japanese Patent Application No. 2013-008648, filed Jan. 21, 2013 is expressly incorporated by reference herein.

TECHNICAL FIELD

The present invention relates to a magnetic field measurement apparatus utilizing light beams.

BACKGROUND ART

A magnetic field measurement apparatus utilizing light beams includes, for example, apparatus configured to measure fine magnetic fields such as magnetic fields from hearts (magnetocardiogram) or magnetic fields from brains (magnetoencephalogram), and is expected to be applied to medical image diagnostic devices. A medium which causes polarization in magnetic moment is used for measurement of the magnetic fields. The medium used here includes a solid element such as diamond provided with lattice defect by nitrogen, and a gas cell in which gas such as alkali metal atoms is encapsulated. Energy of the atoms in the element is excited depending on the magnetic field by irradiation of the element with a pump beam, and a plane of polarization of a probe beam passing through the element is rotated by a magnetooptic effect. The magnetic field measurement apparatus measures the angle of rotation of the plane of polarization as magnetic field information. In Patent Document 1, a magnetic field gradient magnetometer including a transverse light beam pumping system combined thereto is described.

CITATION LIST

Patent Document

[Patent Document 1] JP-A-2009-162554

SUMMARY OF INVENTION

Problems to be Solved by the Invention

However, the magnetic field gradient magnetometer of the system disclosed in Patent Document 1 is configured to measure the magnetic field gradient in a y-direction indicated in a drawing in the same Patent Document, and is not configured to measure the magnetic field gradient in an x-direction. In other words, the magnetic field gradient magnetometer of the system disclosed in Patent Document 1 has no capability of measuring the magnetic field gradient in a direction along the probe beam.

The magnetic field gradient magnetometer of the system disclosed in Patent Document 1 requires a half-wave plate and an optical system configured to generate a circularly-polarized pump beam, and hence is complicated and expensive.

The present invention provides a technology for measuring a magnetic field gradient in a direction along a probe beam with a simpler configuration than that of the related art.

Means for Solving the Problems

In order to solve the above-described problem, the prevent invention provides a magnetic field measurement apparatus including: a probe beam irradiating unit configured to radiate a probe beam; a first medium arranged on an optical axis of the probe beam and showing a linear dichroism with respect to the probe beam between a first axis and a second axis; a second medium arranged on the optical axis of the probe beam on the opposite side of the irradiating unit with respect to the first medium, and showing a linear dichroism with respect to the probe beam between a third axis and a fourth axis, which are different from the first axis and the second axis; and a measuring unit configured to measure a difference between a magnetic field in the first medium and a magnetic field in the second medium on the basis of amounts of change of a plane of polarization of the probe beam that has passed through the first medium and the second medium.

In this configuration, measurement of a magnetic field gradient in a direction along probe beam is achieved with a simpler configuration than that of the related art.

The mode described above preferably includes: a first irradiating unit configured to irradiate the first medium with a first pump beam; and a second irradiating unit configured to irradiate the second medium with a second pump beam, and the first medium includes an atom group composed of a plurality of atoms excited by the first pump beam in the interior thereof, and the second medium includes an atom group composed of a plurality of atoms excited by the second pump beam in the interior thereof.

In this configuration, measurement of a magnetic field gradient in a direction along probe beam is achieved by adjusting the pump beams with which the respective media are irradiated.

Preferably, in the mode described above, the first irradiating unit radiates the first pump beam in a direction which is not in parallel to the direction in which the second irradiating unit radiates the second pump beam.

In this configuration, the pump beams with which the respective media are irradiated may be adjusted.

Preferably, the mode described above includes: a beam splitter arranged at a position interposed between the first medium and the second medium, and configured to separate a radiated light beam and generate a first pump beam that travels toward the first medium and a second pump beam that travels toward the second medium; and a third irradiating unit configured to irradiate the beam splitter with the light beam, and the first medium includes an atom group composed of a plurality of atoms excited by the first pump beam in the interior thereof, and the second medium includes an atom group composed of a plurality of atoms excited by the second pump beam in the interior thereof.

In this configuration, the light beam to be radiated may be one.

Preferably, the mode described above includes: a plurality of beam splitters arranged at positions interposed between the first medium and the second medium, and configured to separate a radiated light beam and generate a first pump beam that travels toward the first medium and a second pump beam that travels toward the second medium; a plurality of third irradiating units provided in one-to-one correspondence with the plurality of beam splitters, and configured to irradiate the corresponding beam splitters with the light beams; and a modulating unit configured to modulate intensities of the respective light beams irradiated by the respective third irradiating units, and the first medium includes an atom group composed of a plurality of atoms excited by the first pump beam in the interior thereof, the second medium includes an atom group composed of a plurality of atoms excited by the second pump beam in the interior thereof, the respective first pump beams generated by the respective beam splitters have a predetermined phase difference, the respective second pump beams generated by the respective beam splitters have the phase difference, and the modulating unit modulates intensities of the respective light beams at frequencies depending on the phase difference.

In this configuration, the range of measurement of the magnetic field may be enlarged.

MODES FOR IMPLEMENTING THE INVENTION

1. First Embodiment
1-1. Configuration

Figure 1A:
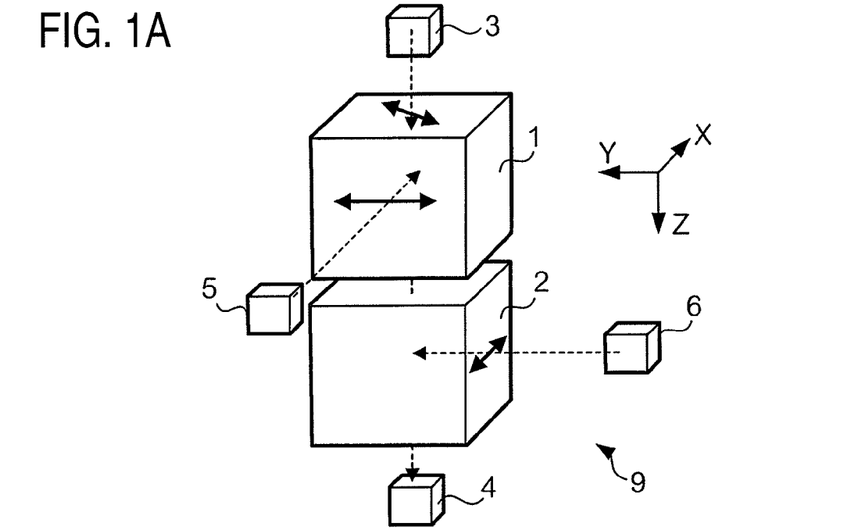
FIGS. 1A, 1B, and 1C are drawings illustrating a general configuration of a magnetic field measurement apparatus of a first embodiment of the present invention.
Figure 1B:
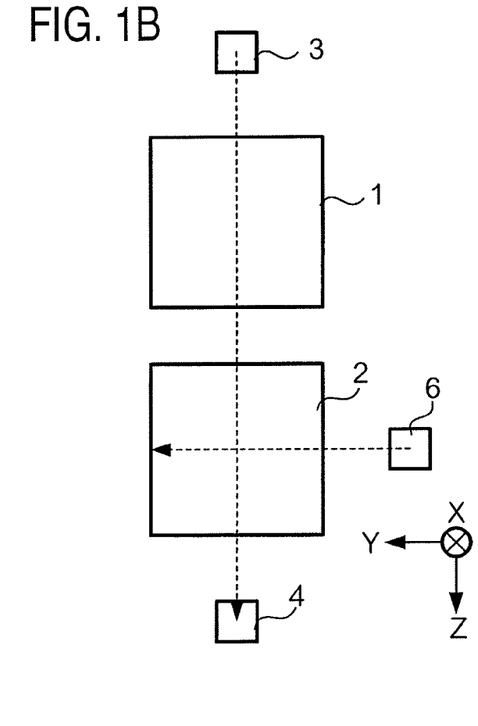
Figure 1C:
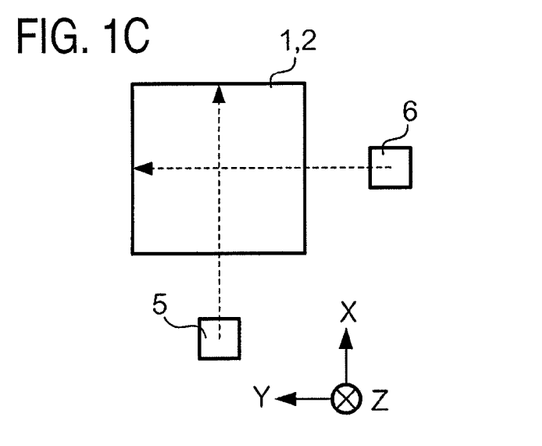

FIG. 1 is a drawing illustrating a general configuration of a magnetic field measurement apparatus 9 of a first embodiment of the present invention. Hereinafter, in order to explain arrangements of respective configurations in the magnetic field measurement apparatus 9, a space in which the respective configurations are arranged is expressed as a XYZ left-handed system coordinate space. Also, signs of a hollow circle with two intersecting segments each represent an arrow directed from the near side to the far side of the paper. In the space, a direction along an X-axis is referred to as X-axis direction. In the X-axis direction, a direction in which an X component increases is referred to as +X direction, and a direction in which the X component decreases is referred to as −X direction. Y-axis direction, +Y direction, −Y direction, Z-axis direction, +Z direction, and −Z direction are defined also for Y and Z components in the same manner.

The magnetic field measurement apparatus 9 includes a gas cell 1 and a gas cell 2 arranged in the +Z direction of the gas cell 1, and also includes a first irradiating unit 5 configured to irradiate the gas cell 1 with a pump beam (hereinafter, referred to as first pump beam), and a second irradiating unit 6 configured to irradiate the gas cell 2 with a pump beam (hereinafter, referred to as second pump beam). The magnetic field measurement apparatus 9 further includes a probe beam irradiating unit 3 configured to irradiate a probe beam along a direction of alignment of the gas cell 1 and the gas cell 2 (hereinafter, referred to simply as "gas cell" when these are not to be discriminated), that is, in the +Z direction, and a measuring unit 4 configured to receive the probe beams that have passed through these gas cells, detect changes of planes of polarization thereof, and measure an intensity differential between a magnetic field in the gas cell 1 (hereinafter, referred to as first magnetic field) and a magnetic field in the gas cell 2 (hereinafter, referred to as second magnetic field).

The two gas cells are glass cells (elements) each including an atom group composed of a plurality of gaseous atoms excited by a pump beam encapsulated therein. Here, the term "gaseous atoms" includes, for example, alkali metal atoms such as potassium (K), rubidium (Rb), or cesium (Cs). These gaseous atoms have a property as a medium for causing the plane of polarization of a light beam passing therethrough to rotate in accordance with an intensity of the magnetic field. The gas cell allows passage of a probe beam radiated from the probe beam irradiating unit 3 therethrough. The probe beam that has passed through the gas cell is received by the measuring unit 4. The material of the gas cell is not limited to glass, and maybe a resin as long as it is a material which allows passage of light beams.

The probe beam irradiating unit 3 is a laser beam output apparatus configured to output laser beams having frequencies corresponding to transition of ultrafine structure level of the atoms encapsulated in the gas cell 1 and the gas cell 2 as probe beams. For example, the wavelength of this laser beam is a wavelength corresponding to the transition of a quantum number of ultrafine structures of a cesium D1 beam encapsulated in the gas cell from F=4 to F'=3, and is approximately 894 nm.

The probe beam irradiating unit 3 is arranged in the −Z direction when viewed from the gas cell 1, and is configured to irradiate the gas cell 1 with a probe beam traveling in the +Z direction. The gas cell 2 is arranged in the +Z direction when viewed from the gas cell 1, and is configured to be irradiated with the probe beam that has passed through the gas cell 1, and allow the same to pass therethrough. Therefore, the gas cell 1 is an example of a medium arranged on an optical axis of the probe beam, and the gas cell 2 is an example of a medium arranged on the optical axis of the probe beam on a downstream side of the gas cell 1, that is, on a side opposite to the probe beam irradiating unit 3 with respect to the gas cell 1. The probe beam irradiating unit 3 is an example of an irradiating unit configured to radiate a probe beam that passes continuously through the gas cell 1 and the gas cell 2.

The first irradiating unit 5 is arranged in the −X direction when viewed from the gas cell 1, and is configured to irradiate the gas cell 1 with the first pump beam, which is a linearly-polarized light beam traveling in the +X direction and vibrating along the Y-axis direction.

The second irradiating unit 6 is arranged in the −Y direction when viewed from the gas cell 2, and is configured to irradiate the gas cell 2 with the second pump beam, which is a linearly-polarized light beam traveling in the +Y direction and vibrating along the X-axis direction.

1-2. Actions

When the gaseous atoms encapsulated in the gas cell are irradiated with a linearly-polarized light beam, the gaseous atoms are subjected to optical pumping, and a probability distribution of magnetic moment generated when energy changes is changed from a spherical origin symmetry distribution. For example, at the time of energy transition F->F'->F−1 of the quantum number of ultrafine structures, the probability distribution of magnetic moment of the gaseous atoms draws a shape following a region extending along the direction of a vibration of the linearly-polarized light beam thereof. This biased probability distribution is referred to as alignment. The alignment rotates by an angle in accordance with the intensity of the magnetic field about an axis of rotation, which corresponds to the direction of the magnetic field. A probe beam passing through the alignment is subjected to absorption of a component more in the direction perpendicular to the alignment than along the direction of the alignment and, consequently, the plane of polarization rotates.

Figure 2:
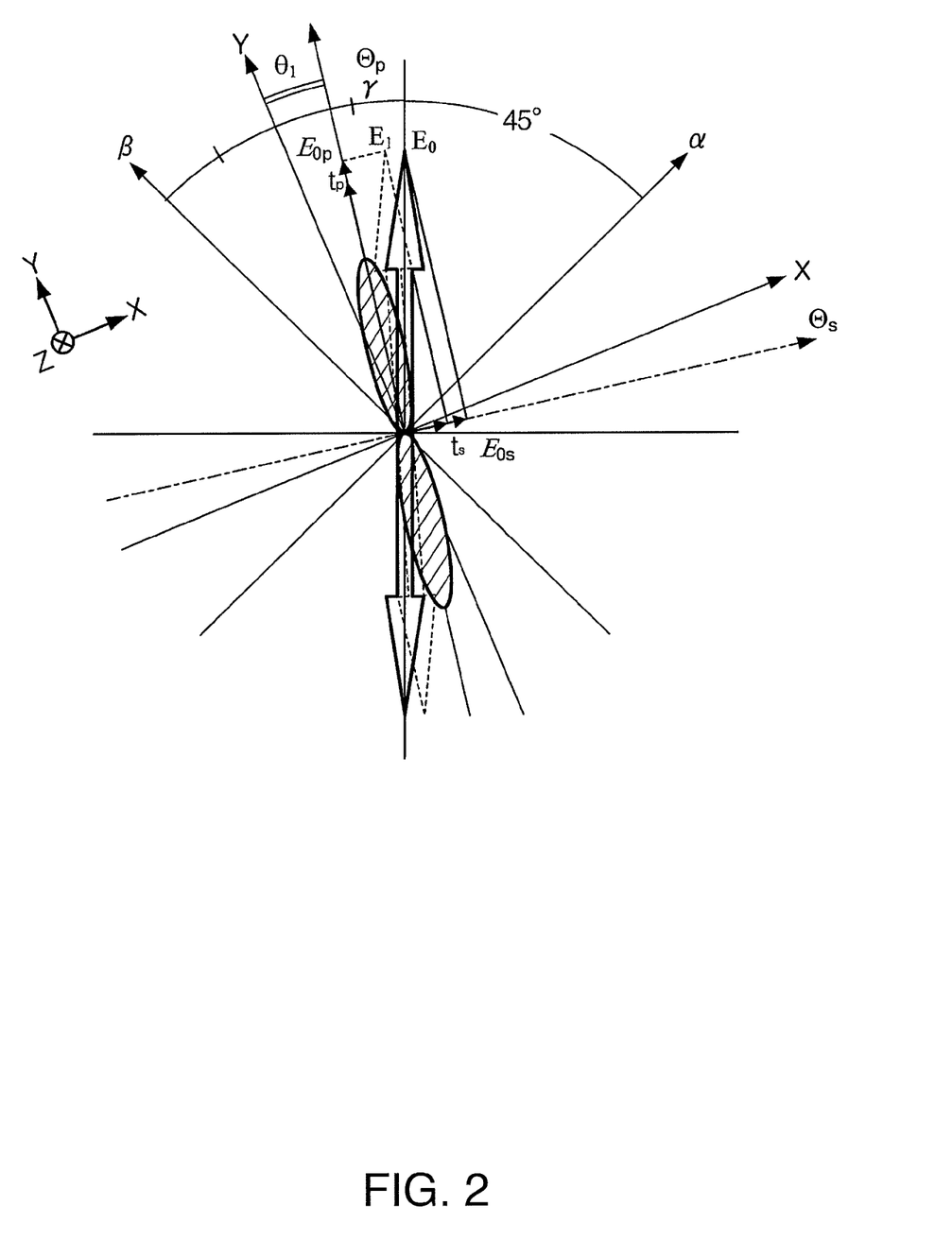
FIG. 2 is a drawing illustrating alignment in the interior of a gas cell 1 and a state of a probe beam.

FIG. 2 is a drawing illustrating alignment in the interior of the gas cell 1 and a state of a probe beam. When the first pump beam is radiated from the first irradiating unit 5, the alignment occurs in the gaseous atoms in the gas cell 1. In the gas cell 1, assuming that the intensity of the magnetic field in the Z-axis direction is "0", the alignment which has occurred does not rotate about the Z-axis as the axis of rotation, and hence extends along the Y direction, which corresponds to the direction of vibrations of the first pump beam. Actually, since the gas cell 1 is in the first magnetic field in the Z-axis direction, the alignment performs precession about the Z-axis as the axis of rotation. With the optical pumping action caused by the first pump beam and an alleviating action caused, for example, by the atoms hitting against an inner wall of the cell, the alignment is brought into a stationary state at a position rotated by an angle ($\theta_1$) in accordance with the intensity of the first magnetic field with respect to the Y-axis. A direction that the alignment faces at this time is defined as $\Theta p$. The alignment rotates clockwise about the Z-axis as the axis of rotation when viewed along the +Z direction in accordance with the intensity of the first magnetic field in the +Z direction.

The sign $\Theta s$ represents a direction perpendicular to $\Theta p$, which is the direction of the alignment on a XY plane. The plane of polarization of the probe beam traveling in the +Z direction is affected by the alignment. The gas cell 1 shows linear dichroism by the alignment. The linear dichroism is a property in which the transmissivity of the linearly-polarized light beam is different between the direction along the alignment and the direction perpendicular to the alignment. Specifically, since the component in the direction perpendicular to the alignment (second axis: direction of $\Theta s$) is absorbed more than that in the direction along the alignment (first axis: direction of $\Theta p$), the plane of polarization of the probe beam rotates so as to get closer to the direction along the alignment. In other words, the gas cell 1 shows the linear dichroism with respect to the probe beam between the first axis and the second axis described above.

For example, as illustrated in FIG. 2, when the vibration of the probe beam entering the gas cell 1 occurs along a vector E0, the alignment allows passage of components of the probe beam along $\Theta p$ at a transmissivity of tp, and allows passage of components thereof along $\Theta s$ at a transmissivity of ts. Since a relationship ts<tp is satisfied because of its linear dichroism, the plane of polarization of the probe beam that has passed through the gas cell 1 rotates so as to get closer to the direction along the alignment, and hence extends along a vector E1.

Here, when it is assumed that "E0" represents an absolute value of the vector E0, which represents the vibration of a probe beam before entering the gas cell 1, "γ" represents an angle of the vector E0 with respect to the Y-axis, and $\theta_1$ represents an angle of rotation in accordance with the intensity of the first magnetic field in the +Z direction of the alignment, respective components in a coordinate system ($\Theta s$, $\Theta p$) of the vector E1, which represents the vibration of the probe beam after the passage through the gas cell 1, are calculated by the following expression (1).

[Expression 1]

$$E_1 = (0 \ E_0)\begin{pmatrix} \cos(\gamma+\theta_1) & \sin(\gamma+\theta_1) \\ -\sin(\gamma+\theta_1) & \cos(\gamma+\theta_1) \end{pmatrix}\begin{pmatrix} t_s & 0 \\ 0 & t_p \end{pmatrix} \quad (1)$$

Figure 3:
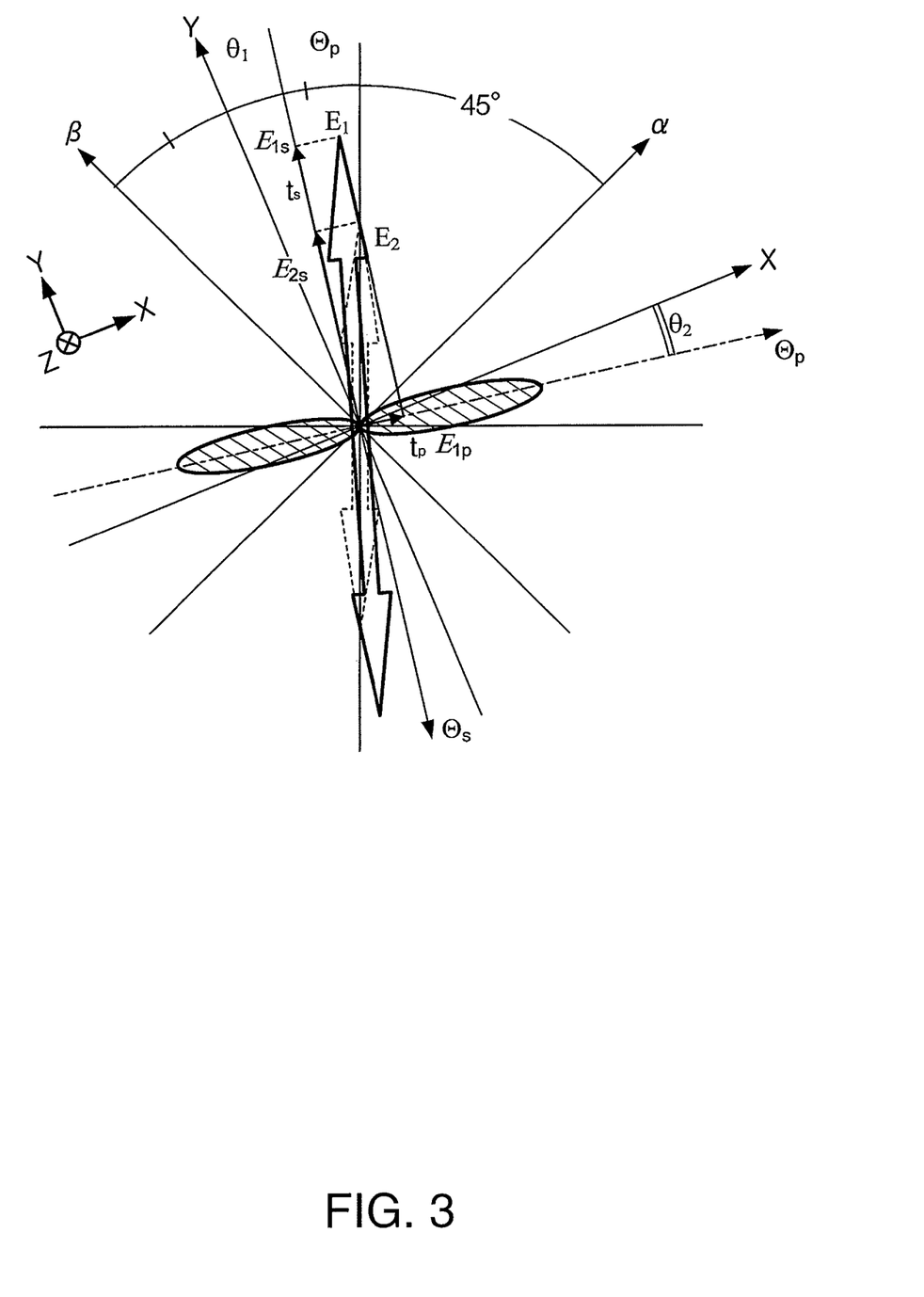
FIG. 3 is a drawing illustrating alignment in the interior of a gas cell 2 and a state of a probe beam.

FIG. 3 is a drawing illustrating alignment in the interior of the gas cell 2 and a state of a probe beam. When the second pump beam is radiated from the second irradiating unit 6, the alignment occurs in the gaseous atoms in the gas cell 2. The gas cell 2 shows linear dichroism by the alignment. In the gas cell 2, assuming that the intensity of the magnetic field in the Z-axis direction is "0", the alignment that has occurred does not rotate about the Z-axis as the axis of rotation, and hence extends along the X direction, which corresponds to the direction of vibrations of the second pump beam. Actually, since the gas cell 1 is in the second magnetic field in the Z-axis direction, the alignment performs precession about the Z-axis as the axis of rotation. With the optical pumping action caused by the second pump beam and an alleviating action, for example, caused by the atoms hitting against an inner wall of the cell, the alignment is brought into a stationary state at a position rotated by an angle ($\theta_2$) in accordance with the intensity of the second magnetic field with respect to the X-axis. A direction that the alignment faces at this time is defined as $\Theta p$, and a direction perpendicular to the $\Theta p$ in the XY plane is defined as $\Theta s$.

As illustrated in FIG. 3, the probe beam after the passage through the gas cell 1 enters the gas cell 2, and the vibration occurs along the vector E1. As described above, the alignment allows passage of components of the probe beam along $\Theta p$ (third axis) at a transmissivity of tp, and allows passage of components thereof along $\Theta s$ (fourth axis) at a transmissivity of ts. Since a relationship ts<tp is satisfied because of its linear dichroism, the plane of polarization of the probe beam that has passed through the gas cell 2 rotates so as to get closer to the direction along the alignment, and hence extends along a vector E2. In other words, the gas cell 2 shows the linear dichroism with respect to the probe beam between the third axis and the fourth axis, which are different from the first axis and the second axis described above.

Here, the direction of vibration of the probe beam is changed from the vector E0 to the vector E1 by the passage through the gas cell 1 as illustrated in FIG. 2, and a counterclockwise rotation results when viewed along the +Z direction. In contrast, the direction of vibration of the probe beam is changed from the vector E1 to the vector E2 by the passage through the gas cell 2 as illustrated in FIG. 3, and a clockwise rotation, which is an opposite direction from that occurring when passing through the gas cell 1, results when viewed along the +Z direction. The reason is that the alignment in the gas cell 1 and the alignment in the gas cell 2 occur respectively so as to interpose the direction of vibration of the probe beam therebetween and rotate the plane of polarization of the probe beam in directions opposite to each other. In other words, the gas cell 1 is a medium existing in the first magnetic field and configured to rotate the plane of polarization passing therethrough in accordance with the intensity of the first magnetic field, and the gas cell 2 is a medium existing in the second magnetic field and configured to rotate the plane of polarization of the light beam passing therethrough in a second direction opposite to the first direction in accordance with the intensity of the second magnetic field.

Assuming that θ2 is an angle of rotation in accordance with the intensity of the second magnetic field in the +Z direction of the alignment in the gas cell 2, the coordinate system ($\Theta s$, $\Theta p$) of the gas cell 2 is rotated clockwise by ($\pi/2-\theta_1+\theta_2$) with respect to the coordinate system ($\Theta s$, $\Theta p$) of the gas cell 1. Therefore, respective components in the ($\Theta s$, $\Theta p$) coordinate system of the vector E2, which represents the vibration of the probe beam after the passage through the gas cell 2, are calculated by the following expression (2).

[Expression 2]

$$E_2 = E_1 \begin{pmatrix} \cos(\pi/2 - \theta_1 + \theta_2) & \sin(\pi/2 - \theta_1 + \theta_2) \\ -\sin(\pi/2 - \theta_1 + \theta_2) & \cos(\pi/2 - \theta_1 + \theta_2) \end{pmatrix} \begin{pmatrix} t_s & 0 \\ 0 & t_p \end{pmatrix} \quad (2)$$

An α axis illustrated in FIG. 3 is an axis obtained by rotating the direction of vibration of the probe beam radiated from the probe beam irradiating unit 3 and before entering the gas cell 1 clockwise by π/4 (that is, 45°) when viewed along the +Z direction. A β axis is an axis obtained by rotating the direction of vibration of the probe beam before entering the gas cell 1 counter clockwise by π/4 (that is, 45°) when viewed along the +Z direction. Therefore, the α axis and the β axis extend orthogonal to each other.

The measuring unit 4 separates the probe beam that has passed through the gas cell 2 into a component along the α axis and a component along the β axis by a polarization beam splitter, by a combination of a Wollaston prism and a photo detector, or the like, measures the light intensities of the respective components, and outputs signals in accordance with the sum and the difference of these components. The vector E2 calculated by the above-described expression (2) is expressed by the (Θs, Θp) coordinate system of the gas cell 2, and the (α, β) coordinate system rotates clockwise by (−3π/4−γ−θ2) from the (Θs, Θp) coordinate system of the gas cell 2. Therefore, assuming that Eα is the light intensity of the component along the α axis and β is the light intensity of the component along the β axis, these values are calculated by the following expression (3).

[Expression 3]

$$(E_\alpha \ E_\beta) = E_2 \begin{pmatrix} \cos(-3\pi/4 - \gamma - \theta_2) & \sin(-3\pi/4 - \gamma - \theta_2) \\ -\sin(-3\pi/4 - \gamma - \theta_2) & \cos(-3\pi/4 - \gamma - \theta_2) \end{pmatrix} \quad (3)$$

When the expressions (1), (2), and (3) are combined, the values Eα and Eβ are expressed by E0, γ, θ$_1$, θ$_2$, ts, tp described above respectively, and the measuring unit 4 obtains an amount of change from the vector E0 to the vector E2 from actual measured values of the Eα and Eβ and the relationships with respect to the vector E0. On the basis of the amount of change, the measuring unit 4 measures a difference of intensity between a magnetic field in the gas cell 1 and a magnetic field in the gas cell 2.

Here, an angle formed by the direction along the alignment and the direction of vibration of the probe beam is referred to as "alignment angle of orientation".

Assuming that the magnetic field in the Z-axis direction is "0", the alignment in the gas cell 1 is arranged along the Y-axis direction. As described above, assuming that the vector E0 represents the vibration of the probe beam entering the gas cell 1 and γ represents the angle of the vector E0 with respect to the Y-axis, the alignment angle of orientation is γ.

The measuring unit 4 measures the vector E2 which represents the vibration of the probe beam after the passage through the gas cell 2 by the (α, β) coordinate system expressed by the α axis and the β axis described above, calculates a square sum W$_+$ and a square difference W$_−$ of respective components extending along the α axis and the β axis, respectively, and outputs the same as shown by the following expression (4).

[Expression 4]

$$W_+ = ED_\alpha{}^2 + E_\beta{}^2$$

$$W_- = E_\alpha{}^2 - E_\beta{}^2 \quad (4)$$

Figure 4:
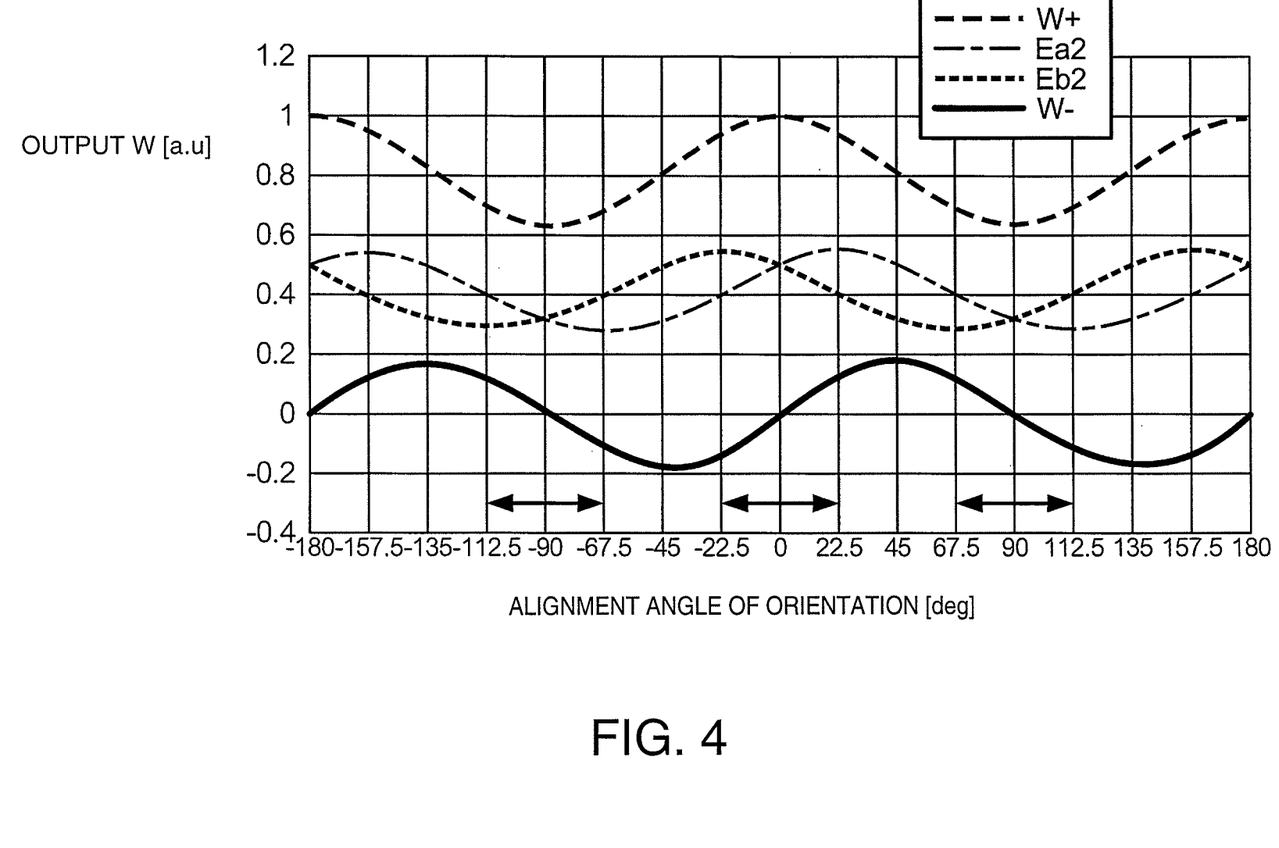
FIG. 4 is a drawing illustrating the relationship between the alignment angle of orientation and the output of a measuring unit.

FIG. 4 is a drawing illustrating the relationship between the alignment angle of orientation γ and the output of the measuring unit 4. FIG. 4 illustrates changes of the square sum W$_+$ and the square difference W$_−$ with respect to the alignment angle of orientation on the presumption that the magnetic field in the Z-axis direction is "0". It is understood from the result illustrated in FIG. 4 that the signal of the square difference W$_−$ vibrates at a cycle of π (180°) with respect to the alignment angle of orientation γ.

When the alignment angle of orientation γ is, for example, within any one of ranges from −112.5° to −67.5°, from −22.5° to 22.5°, and from 67.5° to 112.5°, illustrated in FIG. 4, a signal (output) of the square difference W$_−$ with respect to the alignment angle of orientation γ (input) has a substantially linear shape, and an absolute value of a secondary differentiation (inclination) is larger than those in other ranges. In other words, in these ranges, a ratio of change of the square difference W$_−$ with respect to the change of the alignment angle of orientation γ is higher than other ranges.

Therefore, by adjusting the plane of polarization of the probe beam radiated from the probe beam irradiating unit 3 so that the alignment angle of orientation γ falls within these ranges, the change of the square difference W$_−$ allows the angle of rotation of the alignment in accordance with the intensity of the magnetic field in the Z-axis direction to be monitored by at a high degree of sensitivity.

As described thus far, the magnetic field measurement apparatus 9 described in the first embodiment is simple in structure because the pump beam and the probe beam are linearly-polarized light beam, and no wave plate is required. In the magnetic field measurement apparatus 9, the directions of rotation of the probe beam passing therethrough is cancelled each other out by the gas cell 1 and the gas cell 2, so that measurement of the magnetic field gradient in the direction along the probe beam is achieved by comparing the probe beam before passing through the gas cell 1 and the probe beam after the passage through the gas cell 2.

The angle γ with respect to the Y-axis of the vector E0 described above is not specifically limited as long as the measuring unit 4 can obtain the amount of change from the vector E0 to the vector E2, but angles of 22.5 and 67.5 are preferable. This is because the detection sensitivity of the amount of change described above is improved by setting the angle γ to these angles in comparison with the case of being set to other angles.

2. Second Embodiment

Figure 5A:
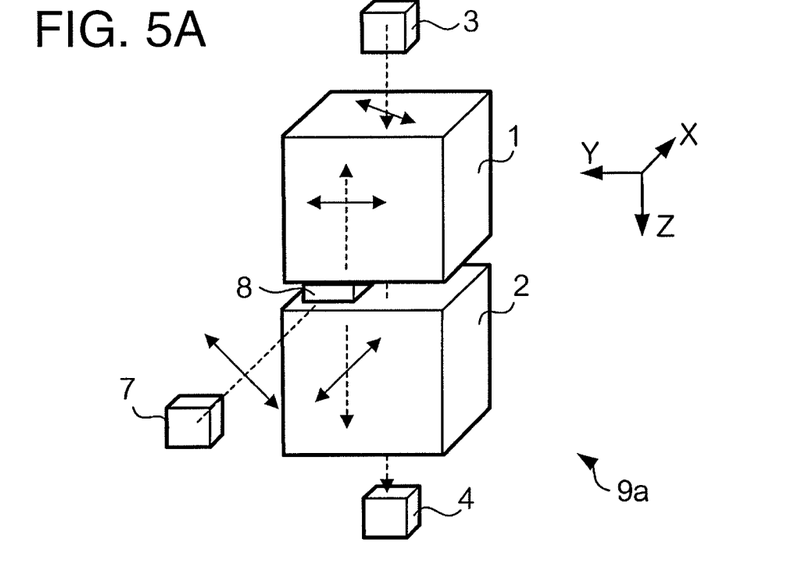
FIGS. 5A and 5B are drawings illustrating a general configuration of a magnetic field measurement apparatus of a second embodiment of the present invention.
Figure 5B:
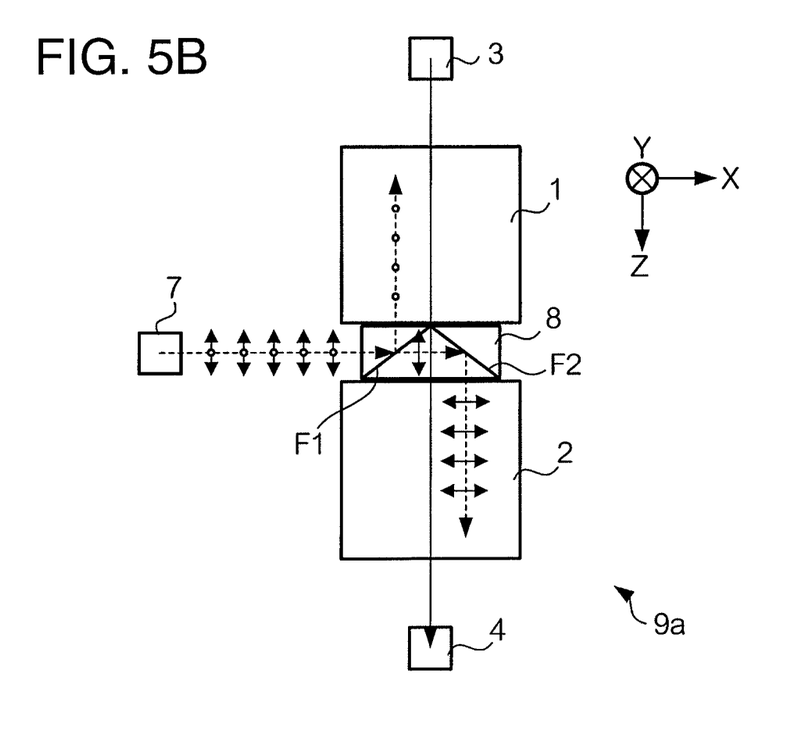

FIG. 5 is a drawing illustrating a general configuration of a magnetic field measurement apparatus 9a of a second embodiment of the present invention. The magnetic field measurement apparatus 9a is common to the magnetic field measurement apparatus 9 described above in having the gas cell 1, the gas cell 2, the probe beam irradiating unit 3, and the measuring unit 4. However, the magnetic field measurement apparatus 9a does not include the first irradiating unit 5 and the second irradiating unit 6, and includes a third irradiating unit 7 and a beam splitter 8.

As illustrated in FIG. 5(a), the beam splitter 8 is arranged at a position interposed between the gas cell 1 and the gas cell 2, and is configured to separate a radiated light beam and generate two light beams traveling respectively in the +Z direction and −Z direction. The third irradiating unit 7 is arranged in the −X direction when viewed from the beam splitter 8, and is configured to irradiate the beam splitter 8 with a light beam traveling in the +X direction. A light beam that the third irradiating unit 7 radiates is a light beam vibrating at an inclination of $\pi/4$ (45°) with respect to the Y-axis direction.

When viewed along the Y-axis, the beam splitter 8 includes a surface F1 and a surface F2 as illustrated in FIG. 5(*b*). The surface F1 has the same function as a polarized light beam splitter. In other words, the surface F1 reflects S-polarized light beam in the direction of the gas cell 1 (−Z direction) and transmits P-polarized light beam among the light beams radiated by the third irradiating unit 7. The surface F2 reflects the P-polarized light beam that passed through the surface F1 totally in the direction of the gas cell 2 (+Z direction). Accordingly, since the gas cell 1 is irradiated with the first pump beam vibrating along the Y-axis direction and the gas cell 2 is irradiated with the second pump beam vibrating along the X-axis direction, the same light beam pumping effect as in the first embodiment described above is achieved.

3. Third Embodiment

Figure 6A:
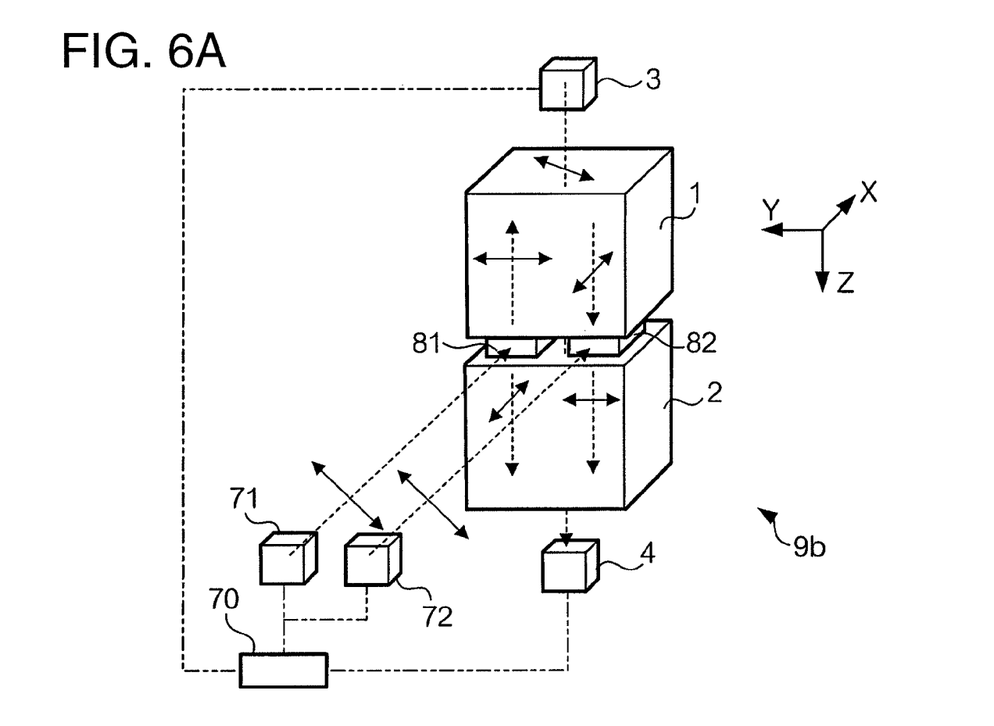
FIGS. 6A and 6B are drawings illustrating a general configuration of a magnetic field measurement apparatus of a third embodiment of the present invention.
Figure 6B:
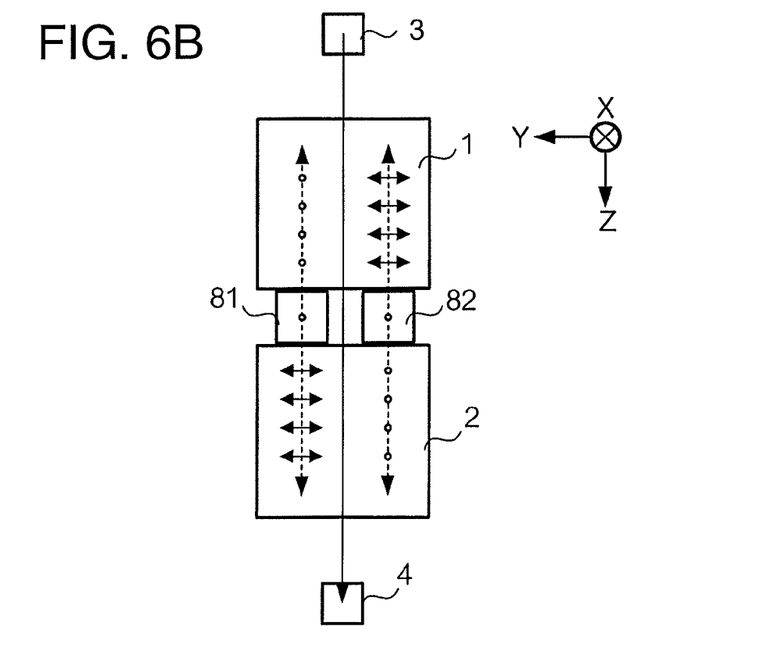

FIG. 6 is a drawing illustrating a general configuration of a magnetic field measurement apparatus 9*b* of a third embodiment of the present invention. The magnetic field measurement apparatus 9*b* is common to the magnetic field measurement apparatus 9 and the magnetic field measurement apparatus 9*a* described above in having the gas cell 1, the gas cell 2, the probe beam irradiating unit 3, and the measuring unit 4. However, the magnetic field measurement apparatus 9*b* does not include the first irradiating unit 5 and the second irradiating unit 6.

The magnetic field measurement apparatus 9*b* includes a plurality of irradiating units, that is, a fourth irradiating unit 71 and a fifth irradiating unit 72 instead of the third irradiating unit 7 provided solely in the magnetic field measurement apparatus 9*a*, and further includes a modulating unit 70 configured to control the fourth irradiating unit 71 and the fifth irradiating unit 72 and configured to change the intensity of a light beam to be radiated.

The magnetic field measurement apparatus 9*b* includes a plurality of bam splitters, that is, a first beam splitter 81 and a second beam splitter 82 instead of the beam splitter 8 which is solely provided in the magnetic field measurement apparatus 9*a*.

As illustrated in FIG. 6(*a*), the first beam splitter 81 and the second beam splitter 82 are both arranged at positions interposed between the gas cell 1 and the gas cell 2. These beam splitters are configured to separate a radiated light beam and generate two light beams traveling respectively in the +Z direction and −Z direction.

The first beam splitter 81 and the second beam splitter 82 both have the same configuration as the beam splitter 8 described in conjunction with the magnetic field measurement apparatus 9*a*, but are arranged reversely in the vertical direction (Z-axis direction). Therefore, assuming that, for example, the first beam splitter 81 causes S-polarized light beam to travel in the direction of the gas cell 2 (+Z direction), and causes P-polarized light beam to travel in the direction of the gas cell 1 (−Z direction), the second beam splitter 82, on the contrary, causes the S-polarized light beam to travel in the direction of the gas cell 1 (−Z direction), and causes the P-polarized light beam to travel in the direction of the gas cell 2. (+Z direction).

The fourth irradiating unit 71 is arranged in the −X direction when viewed from the first beam splitter 81, and is configured to irradiate the first beam splitter 81 with a light beam traveling in the +X direction. A light beam that the fourth irradiating unit 71 radiates is a light beam vibrating at an inclination of $\pi/4$ (45°) with respect to the Y-axis direction.

The fifth irradiating unit 72 is arranged in the −X direction when viewed from the second beam splitter 82, and is configured to irradiate the second beam splitter 82 with a light beam traveling in the +X direction. A light beam that the fifth irradiating unit 72 radiates is a light beam vibrating at an inclination of $\pi/4$ (45°) with respect to the Y-axis direction.

The modulating unit 70 is configured to increase and decrease the intensity of a light beam that the fourth irradiating unit 71 radiates and the intensity of a light beam that the fifth irradiating unit 72 radiates alternately. The measuring unit 4 calculates an average value of the respective magnetic fields of the gas cell 1 and the gas cell 2, and transmits the calculated average value to the modulating unit 70. The modulating unit 70 receives the average value of the magnetic field from the measuring unit 4. The modulating unit 70 controls a frequency (modulated frequency) that increases and decreases the intensity of a light beam that each of the fourth irradiating unit 71 and the fifth irradiating unit 72 radiates so as to be a frequency (precessional frequency) corresponding to the received average value of the magnetic field. Accordingly, the alignments of the gaseous atoms encapsulated in the gas cell 1 and the gas cell 2 respectively perform precession at a phase difference of $\pi/2$ (90°).

The modulating unit 70 is also configured to modulate the intensity of the probe beam that the probe beam irradiating unit 3 radiates while maintaining the phase difference of $\gamma$ with respect to a light beam that the fourth irradiating unit 71 radiates. The measuring unit 4 of the magnetic field measurement apparatus 9*b* then measures the differential in intensity between the magnetic field in the gas cell 1 and the magnetic field in the gas cell 2 by detection by using a lock-in amplifier with a standard signal of the precessional frequency as a reference signal.

As described thus far, since the pump beam and the probe beam are modulated into the precessional frequency of the gaseous atoms by the modulating unit 70, the range of measurement of the magnetic field may be enlarged.

4. Modification

Although the embodiments have been described thus far, the contents of the embodiments may be modified as follows. Alternatively, the following modifications may be combined.

4-1. Modification 1

In the embodiment described above, the magnetic field measurement apparatus 9 includes a gas cell, which is a glass-made cell (element) in which the gaseous atoms are encapsulated. However, media other than the gaseous atoms may be employed as a medium for rotating the plane of polarization of a transmitting light beam in accordance with the intensity of the magnetic field. For example, the magnetic field measurement apparatus 9 may employ the solid element such as diamond provided with lattice defect by nitrogen as the above-described media.

4-2. Modification 2

In the embodiments described above, the magnetic field measurement apparatus 9 has a configuration in which the probe beam passes through the respective gas cells only once (that is, a single-pass configuration). However, a configuration that allows the probe beam to pass through the gas cells by a plurality of times by causing the probe beam to be reflected by using a mirror (a multi-pass configuration) is also applicable. For example, the magnetic field measurement apparatus 9 may have a configuration in which the probe beam after the passage of the gas cell 2 is reflected by the mirror, the reflected light beam is caused to pass through the gas cell 2 again, and the reflected light beam that has passed is further caused to pass through the gas cell 1 (a double-pass configuration). The number of times of reflection of the probe beam is not limited to once, and twice or more times of reflections may also be employed by arranging optical systems such as a reflection mirror or the like (mirrors) at a plurality of positions. Accordingly, the difference in sensitivity which depends on the amount of an incident light beam of the gas cells 1 and 2 is reduced, so that the sensitiveness of measurement of the magnetic field gradient is improved.

4-3. Modification 3

In the above-described first embodiment, the first pump beam is caused to travel in the X-direction, and the second pump beam is caused to travel in the Y-direction. However, these directions do not have to be orthogonal to each other.

In a word, the first irradiating unit 5 needs only to radiate the first pump beam in a direction which is not in parallel to the direction of the second pump beam radiated by the second irradiating unit 6 and, consequently, act so that the alignment of the gas cell 1 and the alignment of the gas cell 2 are generated respectively so as to interpose the direction of vibration of the probe beam therebetween and cause the plane of polarization of the probe beam to rotate in directions opposite to each other.

4-4. Modification 4

In the third embodiment described above, the magnetic field measurement apparatus 9b includes two each of the irradiating units and the beam splitters. However, three or more each of these members may be provided. In this case as well, what is essential is that the first pump beams with which the beam splitters irradiate the gas cell 1 have phase differences, and the second pump beams with which the beam splitters irradiate the gas cell 2 have phase differences. The modulating unit 70 needs only to modulate the intensities of the respective light beams radiated by the respective irradiating units by frequencies in accordance with the phase differences.

The invention claimed is:

1. A magnetic field measurement apparatus comprising:
   a probe beam irradiating unit comprising optics that radiate a probe beam;
   a first medium arranged on an optical axis of the probe beam and showing a linear dichroism with respect to the probe beam between a first axis and a second axis;
   a second medium arranged on the optical axis of the probe beam on the opposite side of the irradiating unit with respect to the first medium, and showing a linear dichroism with respect to the probe beam between a third axis and a fourth axis, which are different from the first axis and the second axis; and
   a measuring unit comprising at least one sensor that measures a difference between a magnetic field in the first medium and a magnetic field in the second medium on the basis of amounts of change of a plane of polarization of the probe beam that has passed through the first medium and the second medium.

2. The magnetic field measurement apparatus according to claim 1, comprising:
   a first irradiating unit comprising optics that irradiate the first medium with a first pump beam; and
   a second irradiating unit comprising optics that irradiate the second medium with a second pump beam, wherein
   the first medium includes an atom group composed of a plurality of atoms excited by the first pump beam in the interior thereof, and
   the second medium includes an atom group composed of an plurality of atoms excited by the second pump beam in the interior thereof.

3. The magnetic field measurement apparatus according to claim 2, wherein the first irradiating unit radiates the first pump beam in a direction which is not in parallel to the direction in which the second irradiating unit radiates the second pump beam.

4. The magnetic field measurement apparatus according to claim 1, comprising:
   a beam splitter arranged at a position interposed between the first medium and the second medium, and configured to separate a radiated light beam and generate a first pump beam that travels toward the first medium and a second pump beam that travels toward the second medium; and
   a third irradiating unit comprising optics that irradiate the beam splitter with the light beam, wherein
   the first medium includes an atom group composed of a plurality of atoms excited by the first pump beam in the interior thereof, and
   the second medium includes an atom group composed of an plurality of atoms excited by the second pump beam in the interior thereof.

5. The magnetic field measurement apparatus according to claim 1, comprising:
   a plurality of beam splitters arranged at positions interposed between the first medium and the second medium, and configured to separate a radiated light beam and generate a first pump beam that travels toward the first medium and a second pump beam that travels toward the second medium;
   a plurality of third irradiating units provided in one-to-one correspondence with the plurality of beam splitters, and configured to irradiate the corresponding beam splitters with the light beams; and
   a modulator configured to modulate intensities of the respective light beams radiated by the respective third irradiating units, wherein
   the first medium includes an atom group composed of a plurality of atoms excited by the first pump beam in the interior thereof,
   the second medium includes an atom group composed of a plurality of atoms excited by the second pump beam in the interior thereof, the respective first pump beams generated by the respective beam splitters have a predetermined phase difference,
   the respective second pump beams generated by the respective beam splitters have the phase difference, and
   the modulator modulates intensities of the respective light beams at frequencies depending on the phase difference.

6. The magnetic field measurement apparatus according to claim 1, wherein the probe beam irradiating unit comprises a laser.

* * * * *